(12) United States Patent
Brown

(10) Patent No.: US 8,489,341 B2
(45) Date of Patent: Jul. 16, 2013

(54) METHOD AND APPARATUS FOR VOLUMETRIC GAS IN-LINE SENSING

(75) Inventor: Houston Brown, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 598 days.

(21) Appl. No.: 12/142,321

(22) Filed: Jun. 19, 2008

(65) Prior Publication Data

US 2009/0319204 A1 Dec. 24, 2009

(51) Int. Cl.
*G01F 1/56* (2006.01)

(52) U.S. Cl.
USPC ........... 702/47; 702/50; 702/55; 73/19.11; 73/19.1; 73/19.03; 324/670; 324/686; 324/690; 128/DIG. 12; 128/DIG. 13; 422/88; 422/82.01; 422/82.02

(58) Field of Classification Search
USPC ............ 702/47, 52, 50, 55; 73/335.04, 19.1, 73/19.11, 19.03, 304 C, 64.44, 861.53, 149, 73/61.71, 861.95; 324/670, 686, 690, 694; 128/DIG. 12, DIG. 13; 436/149; 422/69, 422/88, 82.01, 82.02, 83, 90
See application file for complete search history.

(56) References Cited

U.S. PATENT DOCUMENTS

| | | | | |
|---|---|---|---|---|
| 4,043,178 A | * | 8/1977 | Winslow, Jr. ................... | 73/23.2 |
| 4,367,736 A | * | 1/1983 | Gupton ........................... | 604/30 |
| 4,565,500 A | * | 1/1986 | Jeensalute et al. ............. | 417/53 |
| 4,710,757 A | | 12/1987 | Haase | |
| 4,752,727 A | * | 6/1988 | Schneider .................... | 324/605 |
| 4,835,456 A | * | 5/1989 | Liu et al. ...................... | 324/674 |
| 5,017,879 A | * | 5/1991 | Lucas et al. ................... | 324/663 |
| 5,394,339 A | * | 2/1995 | Jones ............................... | 702/12 |
| 5,455,565 A | * | 10/1995 | Moeenziai et al. ........... | 340/603 |
| 5,515,713 A | * | 5/1996 | Saugues et al. .............. | 73/19.03 |
| 7,377,148 B2 | * | 5/2008 | Cassidy et al. ................. | 73/19.1 |
| 2003/0020493 A1 | * | 1/2003 | Haase et al. ................... | 324/664 |
| 2006/0037393 A1 | * | 2/2006 | Itakura et al. .............. | 73/335.04 |

FOREIGN PATENT DOCUMENTS

| | | |
|---|---|---|
| DE | 4034471 | 3/1992 |
| EP | 0308004 | 3/1989 |
| EP | 0510774 | 10/1992 |
| GB | 2164450 | 3/1986 |
| GB | 2390683 | 1/2004 |
| WO | WO 2005118051 | 12/2005 |

OTHER PUBLICATIONS

International Search report from PCT/US2009/047820, dated Sep. 18, 2009.

* cited by examiner

*Primary Examiner* — Carol Tsai

(74) *Attorney, Agent, or Firm* — McDermott Will & Emery LLP

(57) ABSTRACT

A method and apparatus for monitoring fluid in a fluid line are disclosed. The apparatus includes a first capacitor and a processor in communication with the first capacitor. The first capacitor is configured to sense the capacitance of the fluid line at the first capacitor. The processor is configured to compare the sensed capacitance at the first capacitor with a reference capacitance to determine the composition of the fluid in the fluid line at the first capacitor. In some embodiments, the apparatus also includes a second capacitor. The second capacitor is configured to sense the capacitance of the fluid line at the second capacitor. The processor is configured to compare the sensed capacitance at the second capacitor with a reference capacitance to determine the composition of the fluid in the fluid line at the second capacitor.

19 Claims, 6 Drawing Sheets

METHOD AND APPARATUS FOR VOLUMETRIC GAS IN-LINE SENSING

FIELD

The present disclosure relates generally to monitoring fluid in a line without direct fluid contact, and more particularly, relates to non-intrusively monitoring for changes in fluid properties, including the presence of air or other gas.

BACKGROUND

In numerous medical and industrial applications, continuous in-line monitoring of a fluid is often necessary to ensure consistency of a process or to ensure safety. For example, the pressure of fluid in a line may be critical to a process. Additionally, the presence of air or other gas within a fluid or the presence of contaminants within a fluid may need to be monitored.

In the medical arena, gas-in-line detection systems are used to prevent the inadvertent infusion of gas into a patient's bloodstream. While small bubbles of gas may have no adverse effect on a patient, large gas bubbles can cause air embolism resulting in pain or death. Methods for the in-line detection of gas typically involve ultrasound or light transmission through the fluid line being monitored. The different transmission characteristics of sound or light through fluids and gases may be utilized to form an indication of the presence of a gas bubble in liquid in the fluid line. Simple recognizable perturbations of the signals from such sensors may be utilized to trigger an alarm and/or halt the infusion. Such systems require that the fluid and the associated conduit be substantially transparent to the energy being transmitted.

In one exemplary implementation, ultrasonic energy in the megahertz (MHz) range is coupled on one side of a conduit under test, and a receiver is placed on the opposite side. When a gas bubble is present in the conduit, energy is attenuated from the transmitted side to the received side. When fluid is present in the conduit, the energy received in the receiver is greatly increased. This energy or signal strength may thus be used as an indicator to determine whether gas is present in the conduit. Additionally, if the fluid rate is known, gas bubble size can be determined and thresholds can be set to indicate when a gas bubble has exceeded a preset limit, thereby triggering an alarm.

However, too often gas bubbles do not travel at the same velocity as the fluid, causing the gas bubbles to be interpreted as larger than they are, generating a false or nuisance alarm. This can be caused by a "Taylor" type bubble or "champagne" bubbles sticking to the side of the conduit, causing sufficient attenuation to cause an alarm. Additionally, ultrasonic or optical gas-in-line detectors typically cannot determine the exact size of gas bubbles and are configured merely to indicate the presence of gas bubbles which are greater than a predetermined size.

Other apparatus capable of detecting impurities such as gas within a fluid include optical systems. However, image processing used in conjunction with such optical systems make this option prohibitively expensive.

SUMMARY

There is a need for an in-line fluid monitoring system and method which do not involve direct fluid contact with a sensor but which exhibit higher sensitivity to variations in fluid composition, including the presence of air or other gas, and which can provide an indication of the size of a gas bubble. In medical systems, there is a need for an apparatus and method which reliably and accurately detect and quantify the presence of gas or other impurities in the line but at the same time are relatively inexpensive and can function with an inexpensive disposable fluid line.

The presently disclosed embodiments are directed to solving one or more of the problems presented in the prior art, described above, as well as providing additional features that will become readily apparent by reference to the following detailed description when taken in conjunction with the accompanying drawings.

One or more preferred embodiments are directed to a method for in-line fluid monitoring without direct fluid contact. Detection of fluid properties, including the presence of air or other gas and the indication of changes in fluid composition is provided. The method comprises passing fluid through a fluid line, wherein the fluid line is at least partially surrounded by a first capacitor, and sensing the capacitance of the fluid line at the first capacitor. The method further comprises comparing the sensed capacitance at the first capacitor with a reference capacitance and determining whether gas is present in the fluid line based on the comparing of the sensed capacitance at the first capacitor to the reference capacitance.

One or more preferred embodiments may include an apparatus for monitoring fluid in a fluid line. The apparatus comprises a first capacitor and a processor in communication with the first capacitor. The first capacitor comprises a first plate and a second plate, the first and second plates being separated by and positioned on opposing sides of the fluid line such that fluid moving through the fluid line passes between the first and second plates. The first capacitor is configured to sense the capacitance of the fluid line. The processor is configured to compare the sensed capacitance at the first capacitor with a reference capacitance to determine the composition of the fluid in the fluid line.

One or more preferred embodiments provide a method for determining gas bubble flow rate in a fluid line. The method comprises passing fluid through a fluid line, wherein the fluid line is at least partially surrounded by a first capacitor and a second capacitor, determining a first time at which a capacitance at the first capacitor falls below a first threshold and determining a second time at which a capacitance at the second capacitor falls below the first threshold. The first and second capacitors are spaced apart from another along the fluid line to define a capacitance monitoring distance. The method further comprises subtracting the determined first time from the determined second time to yield a gas bubble travel time and determining a gas bubble flow rate based on the gas bubble travel time and the capacitance monitoring distance.

One or more preferred embodiments provide a method for determining gas bubble size in a fluid line. The method comprises providing a first capacitor at least partially surrounding a fluid line and having a bore diameter for fluid flow within and detecting the presence of a gas bubble in the fluid line by measuring the capacitance at the first capacitor when the capacitance falls below a threshold. The method further comprises correlating the measured capacitance at the first capacitor with a gas volume based in part on the fluid line bore diameter.

As will become evident by the following Description and Drawings, by accurately determining gas bubble size in the line and/or gas bubble flow rate, the number of false or nuisance alarms generated may be minimized. Furthermore, when an alarm is generated due to a problematic gas bubble size or bubble flow rate, the fluid line may be purged to ensure that a patient does not receive potentially dangerous fluid.

Of course, the present invention is not limited to the aforementioned embodiments, and other features of the embodiments will become apparent after review of the hereinafter set forth Brief Description of the Drawings, Detailed Description, and the Claims, or may be learned by practice of the invention.

BRIEF DESCRIPTION OF THE DRAWINGS

The foregoing aspects of the embodiments described herein will become more readily apparent by reference to the following detailed description when taken in conjunction with the accompanying drawings wherein.

DETAILED DESCRIPTION

Figure 1:
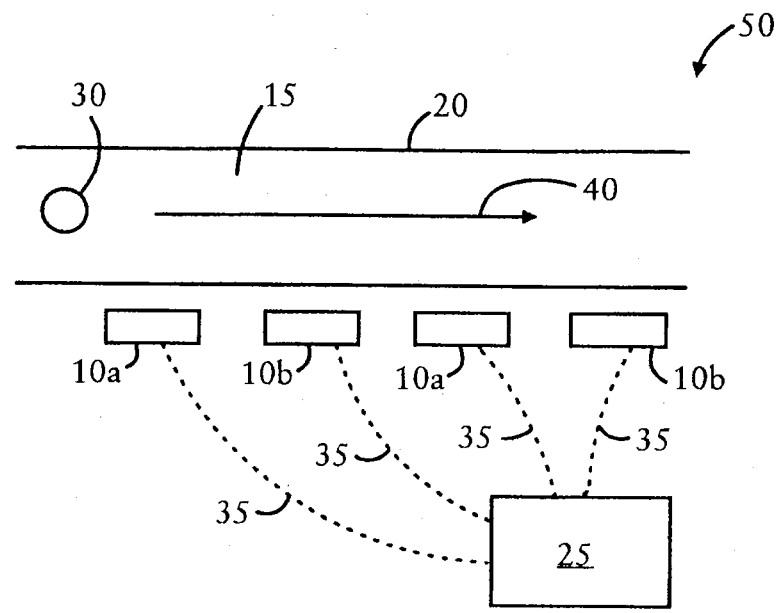
FIG. 1 is a schematic depiction of a capacitor assembly, according to certain disclosed embodiments.

Reference will now be made in detail to the presently disclosed embodiments, examples of which are illustrated in the accompanying drawings, wherein like reference numerals refer to like elements throughout. As used herein, dielectric constant refers to a measure of the ability of a material to resist the formation of an electric field within it. Additionally, dielectric constant and relative permittivity will be used interchangeably when describing the presently disclosed embodiments.

FIG. 1 shows a schematic of one example of a capacitor assembly 50 constructed from a plurality of capacitors 10. It is noted, however, that the disclosed embodiments are not limited to any particular number of capacitors within the capacitance assembly 50.

Each capacitor 10 is made up of two active plates 10$a$ and 10$b$, which are located in the same plane. The capacitance for each capacitor is determined by the following equation:

$$C = Q/V \quad \text{(Eqn. 1)}$$

where C is the capacitance, Q is the amount of charge stored on each plate, and V is the potential difference or voltage which appears between the plates. Capacitance is given in units of Farads (F).

While this capacitance equation is generally used for two plates that are parallel to each other, this capacitance equation may be used as a rough approximation for two plates that are in the same plane. Other capacitance equations may also be used as approximations for determining the capacitance of capacitors 10 in FIG. 1. For example:

$$C \approx \in A/d \quad \text{(Eqn. 2)}$$

where C is the capacitance, $\in$ is the permittivity of the material between two parallel plates, A is the area of each plate, and d is the distance between the two plates.

Referring still to FIG. 1, when an object 15 with a high dielectric constant forms a disturbance between and/or above plates 10$a$, 10$b$, the capacitance of the capacitors 10 is increased. As shown in FIG. 1, object 15 may be a fluid comprising a fluid path 40. A high dielectric constant is herein defined as being greater than or equal to 60 at room temperature.

Applying the concept of FIG. 1 to an in-line fluid monitoring system, fluid path 40 is positioned proximate to plates 10$a$, 10$b$. Fluid path 40 is contained within a fluid line 20 and fluid line 20 is preferably is in direct contact with plates 10$a$, 10$b$. When an object 15 such as fluid fills or is flowing through the fluid line 20, a fairly steady capacitance is sensed by capacitor assembly 50 as determined by electrical circuit 25. This steady capacitance is referred to as the reference capacitance. In one embodiment, electrical circuit 25 is in communication 35 with plates 10$a$, 10$b$ via means such as a wired or wireless connection.

When object 15 such as fluid is not flowing through the fluid line, a decrease in capacitance is sensed by capacitor assembly 50. Similarly, when gas bubbles 30 are present at the sensing location in the fluid line, the resulting decrease in capacitance is sensed by capacitor assembly 50.

Figure 7:
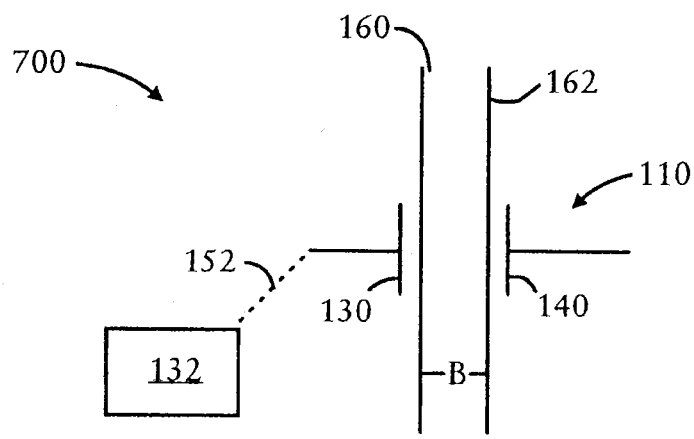
FIG. 7 is a schematic depiction of a fluid monitoring system, according to certain disclosed embodiments.

Referring now to FIG. 7, in this example, a first capacitor 110 comprises a fluid monitoring system 700. First capacitor 110 includes a first plate 130 and a second plate 140. First plate 130 has a length L1 (not shown) and height H1 (not shown). Second plate 140 has a length L2 (not shown) and height H2 (not shown). In some embodiments, second plate 140 length L2 is less than first plate 130 length L1.

As shown in FIG. 7, capacitor 110 surrounds fluid line 160, so that fluid passes by capacitor 110 as the fluid moves through fluid line 160. In other words, fluid passes between the plates 130 and 140. Fluid line 160 generally includes a conduit 162 having a bore of diameter B within conduit 162, such that fluid flows therein. Conduit 162 is preferably fabricated from a flexible material such as a polymer or polymer blend. Suitable materials for conduit 162 include, but are not limited to, silicone, nylon, polyethylene, polyvinyl chloride (PVC), polyurethane, and other known surgical tubing materials. In an exemplary embodiment, conduit 162 is fabricated from PVC.

Figure 8:
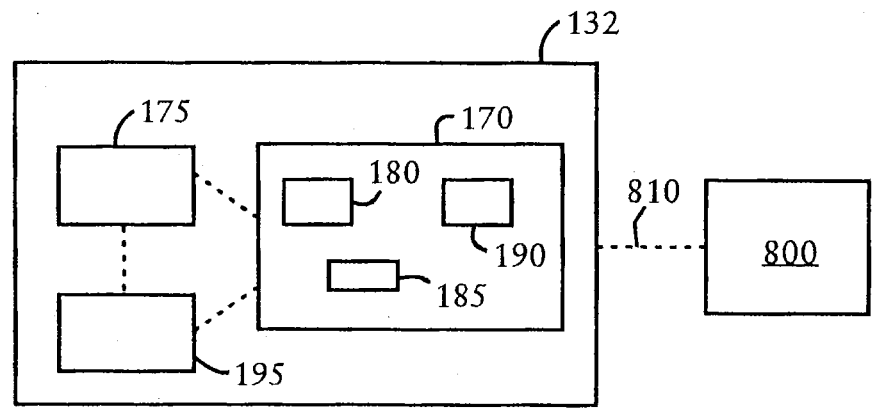
FIG. 8 is a schematic showing an electrical circuit for use in a fluid monitoring system, according to certain disclosed embodiments.

In some embodiments, capacitor 110 is in communication 152 with an electrical circuit 132 which includes a processor 170 and memory 175 (see FIG. 8). Electrical circuit 132 may also include a clock 195 for time stamping. Communication 152 between capacitor 110 and electrical circuit 132 may be achieved by any suitable means including, for example, wired or wireless connections.

Referring briefly to FIG. 8, electrical circuit 132 is shown. Within electrical circuit 132, processor 170 may include a comparator 180, a subtractor 185, a divider 190, and the like. In one embodiment, processor 170 includes components consistent with those typically employed in an arithmetic logic unit (ALU). In some embodiments, electrical circuit 132 performs all calculations for fluid monitoring system 700, as will be discussed below. Furthermore, in some embodiments, electrical circuit 132 is in communication 810 with an alarm 800. In other embodiments, alarm 800 is integral to electrical circuit 132.

As is easily appreciated, the capacitance equations (1) and (2) apply to capacitor 110. However, the calculation of the permittivity E for equation (2) is somewhat complicated by the presence of a plurality of objects between the plates 130 and 140 of capacitor 110. Namely, these objects include: a first wall of conduit 162; fluid flowing within conduit 162; and a second wall of conduit 162.

As stated above, dielectric constant and relative permittivity are used interchangeably when describing the present embodiments. As is known, air has a dielectric constant of approximately 1. PVC has a dielectric constant of approximately 3. Water is temperature sensitive and has a dielectric constant of approximately 80 at room temperature.

Because of the plurality of objects between the plates of capacitor 110, in order to calculate an accurate capacitance due to each of the objects, each object is treated by the system as comprising a separate sub-capacitor. The terms sub-capacitor and sub-capacitance are used herein to differentiate the capacitance from a single object from the combined capacitance from the plurality of objects, as measured by capacitor 110. Thus, the first wall of conduit 162 corresponds to a first sub-capacitor C1, the fluid flowing within conduit 162 corresponds to a second sub-capacitor C2, and the second wall of conduit 162 corresponds to a third sub-capacitor C3.

Still referring to FIG. 7, the plurality of objects between plates 130 and 140 are treated as being in series with each other. Therefore, the sub-capacitors C1, C2, C3 are treated as being in series with each other. As is known, capacitance for capacitors in series is calculated according to the following equation:

$$1/C = 1/C_1 + 1/C_2 \ldots + 1/C_n \quad \text{(Eqn. 3)}$$

Where C is total capacitance, $C_n$ is the capacitance for an individual capacitor, and n is total number of capacitors.

Also useful is the equation for elastance, which is the reciprocal of capacitance and is given in units of Daraf ($F^{-1}$):

$$C^{-1} = C^{-1}_1 + C^{-1}_2 \ldots + C^{-1}_n, \quad \text{(Eqn. 4)}$$

and accordingly:

$$C^{-1} = d_1/A\epsilon_1 + d_2/A\epsilon_2 + d_3/A\epsilon_3 \quad \text{(Eqn. 5)}$$

For calculation purposes, dimensions for conduit 162 will be assumed to be the following: outer diameter of 4 mm, inner diameter of 2.76 mm, and a wall thickness of approximately 0.62 mm, with there being two walls to take into consideration. Additionally, the dielectric constant used will be for PVC.

While the capacitance for each sub-capacitor C1, C2, C3 will be determined, the area of capacitor 110 will be used for exemplary calculation purposes. In an exemplary embodiment, dimensions for plate 140 will be assumed to be the following: H2 is 2 mm and L2 is 8.5 mm. Therefore, plate 140 has an area of 17×10−6 m2. For simplification purposes, plate 130 is also assumed to have the same area as plate 140. This simplification is justifiable in that the capacitance of capacitors is dependent on the shared length of the plates 130 and 140 surrounding the fluid line. Consequently, the edge effects of the plates 130 and 140 will be ignored.

Table 1 lists the parameters used in an exemplary embodiment:

TABLE 1

| Parameter | Value |
|---|---|
| A | $17 \times 10^{-6}$ m$^2$ |
| $d_1$ | $0.62 \times 10^{-3}$ m |
| $d_2$ | $2.76 \times 10^{-3}$ m |
| $d_3$ | $0.62 \times 10^{-3}$ m |
| $\epsilon_1$ | $3 \times 8.85 \times 10^{-12}$ F/m |
| $\epsilon_2$ | $80 \times 8.85 \times 10^{-12}$ F/m |

TABLE 1-continued

| Parameter | Value |
|---|---|
| $\epsilon_3$ | $3 \times 8.85 \times 10^{-12}$ F/m |
| $\epsilon_{2*}$ | $1 \times 8.85 \times 10^{-12}$ F/m |

Where $\epsilon_{2*}$ represents the dielectric constant of air.

Where $\epsilon_{2*}$ represents the dielectric constant of air.

Using the values from Table 1 in Eqn. 5, including $\epsilon_2$ of 80×8.85×10$^{-12}$ F/m for water in the conduit, results in a total capacitance C of 360×10$^{-15}$ F or 360 fF. Additionally, using the values from Table 1 in Eqn. 5, including $\epsilon_{2*}$ of 1×8.85× 10$^{-12}$ F/m for air in the conduit, results in a total capacitance C of 47.4×10$^{-15}$ F or 47.4 fF. Comparing the total capacitance of fluid monitoring system 100 when fluid is flowing within fluid line 160 with the total capacitance when gas such as air is flowing within fluid line 160 reveals a ratio greater than 7. Thus, a difference of approximately 300 fF would have to be measured to determine whether fluid or gas is flowing within fluid line 160 between the capacitor plates 130, 140. Consequently, when fluid flowing through fluid line 160 is used as the reference capacitance, any decrease in capacitance can be attributed to gas bubbles flowing within the fluid. As such, the reference capacitance may be used as a threshold for determining whether gas is present in fluid line 160. Alternatively, the threshold may be selected based on various factors, including the desire to provide a margin of error so that if the system is coupled to alarm 800, alarm 800 is not triggered by having too high of a value for the threshold.

Because the values listed in Table 1 are for an exemplary embodiment, other values may be used to achieve desired results. For example, using larger plates 130 and 140 would result in a larger area A, which would yield a higher capacitance C. Because the capacitance values that are measured are on such a small scale, and residual capacitance from outside sources may influence measurements, higher capacitance values may be preferred in order to accurately realize the capacitance signal.

Figure 4:
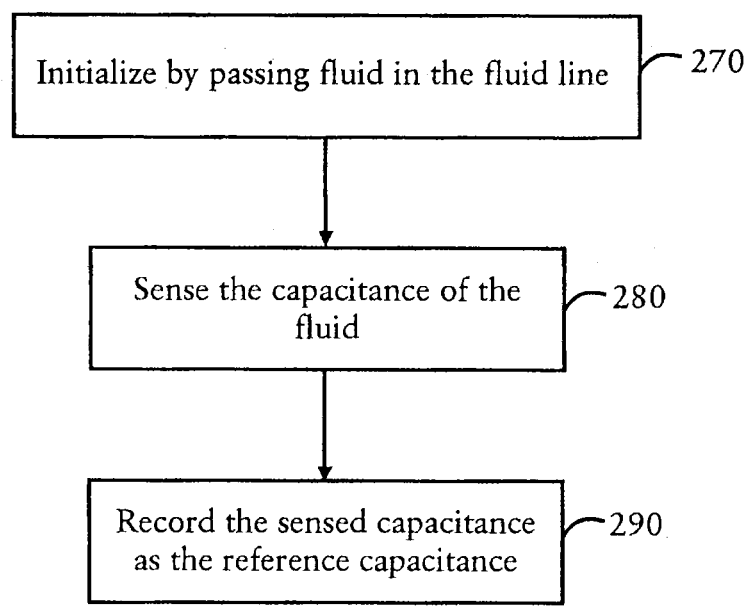
FIG. 4 is a flowchart showing a method for calculating reference capacitance, according to certain disclosed embodiments.

Referring now to FIG. 4, a reference capacitance is calculated. Firstly, fluid is passed through a fluid line 160 in step 270. The capacitance of the fluid is sensed at step 280. The sensed capacitance is then recorded as the reference capacitance at step 290. It should be noted that the fluid passed through the fluid line 160 in FIG. 1 is an initializing fluid, meaning that all gas has been purged from the fluid prior to passing the fluid through the line or that it contains an accepted maximum content of gas. This reference capacitance value is stored to be used later in a comparison step. For example, the reference capacitance value may be stored in memory 175.

Figure 5:
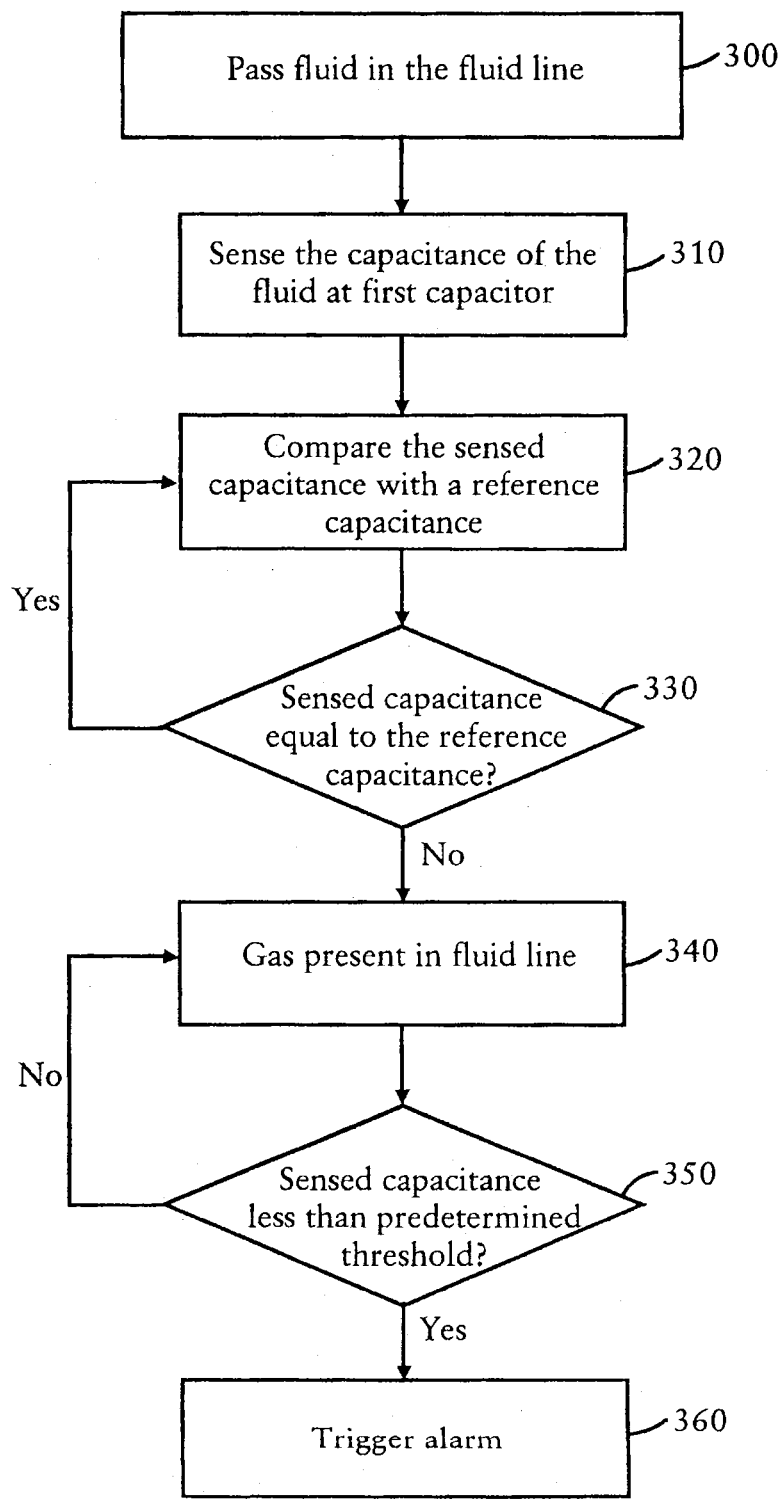
FIG. 5 is a flowchart showing a method for determining the presence of gas in a fluid line, according to certain disclosed embodiments.

Referring now to FIG. 5, fluid is passed through the fluid line 160 at step 300. The capacitance of the fluid is sensed by first capacitor 110 at step 310. At step 320, the capacitance sensed by first capacitor 110 is compared with the reference capacitance value determined at step 290 of FIG. 4. If the sensed capacitance is equal to the reference capacitance as determined at step 330, no gas is detected at that time. If, however, the sensed capacitance is not equal to the reference capacitance, then gas is detected at that time as shown at step 340. If the sensed capacitance is below a threshold as determined at step 350, alarm 800 or other action may be triggered at step 360. If gas is detected, but the sensed capacitance is above the threshold, the alarm 800 will not be triggered.

An example of another action that may be taken if the sensed capacitance is below a threshold at step 350 is stopping the flow of fluid to thereby prevent passage of gas to a patient. Another action may be to notify a caregiver of the gas in the line. Such notification can be performed remotely. Additionally, a combination of these exemplary actions may be performed.

It should be noted that the total capacitance measured in the above example was performed for a single capacitor 110. The use of multiple capacitors would result in multiple total capacitance measurements. See for example, FIG. 2. While not wishing to be bound by any particular theory, it is believed that multiple capacitance measurements aid to preserve the integrity of the capacitance signals.

Figure 2:
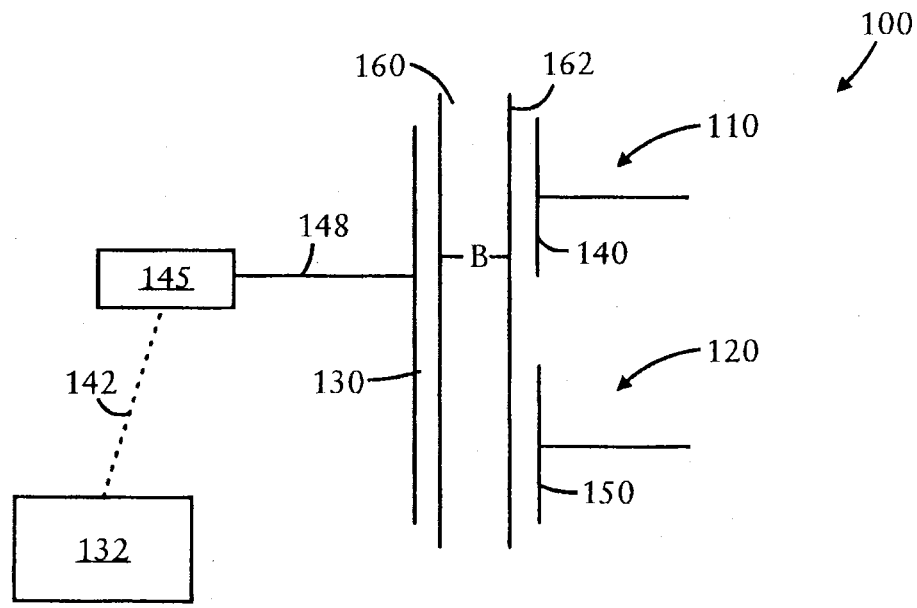
FIG. 2 is a schematic depiction of a fluid monitoring system, according to certain disclosed embodiments.

Referring now to FIG. 2, in this example, first capacitor 110 and a second capacitor 120 comprise a fluid monitoring system 100. First capacitor 110 includes a first plate 130 and a second plate 140. First plate 130 has a length L1 (not shown) and height H1 (not shown). Second plate 140 has a length L2 (not shown) and height H2 (not shown). Second plate 140 length L2 is less than first plate 130 length L1.

Second capacitor 120 includes first plate 130 and a third plate 150. Third plate 150 has a length L3 (not shown) and height H3 (not shown). Third plate 150 length L3 is less than first plate 130 length L1. Hence, first plate 130 is common to the first and second capacitors, 110, 120.

As shown in FIG. 2, capacitors 110 and 120 surround fluid line 160, so that fluid passes between the two capacitors as the fluid moves through fluid line 160. Fluid line 160 generally includes a conduit 162 having a bore of diameter B within conduit 162, such that fluid flows therein.

A benefit of the fluid monitoring systems 100 and 700 is that a standard capacitance-to-digital converter 145 may be employed to implement the capacitance measurements. For example, Analog Devices AD7746 is such a capacitance-to-digital converter that is capable of resolving 10-18 F (aF) and has an absolute error of ±4×−15 F (fF). The AD7746 24-bit, 2 Channel Capacitance to Digital Converter Data Sheet, available at http://www.analog.com/UploadedFiles/Data_Sheets/AD7745_7746.pdf, herein incorporated by reference shows such a device.

Referring still to FIG. 2, capacitance-to-digital converter 145 is shown in communication 142 with electrical circuit 132 and in communication 148 with capacitors 110, 120. Communication 142 between capacitance-to-digital converter 145 and electrical circuit 132 and communication 148 between capacitance-to-digital converter 145 and capacitors 110, 120 may be achieved by any suitable means including, for example, wired or wireless connections. In one embodiment, capacitance-to-digital converter 145 is integral to electrical circuit 132.

In such a system, having two capacitors 110, 120, the differential capacitance may also be determined. The differential capacitance is determined by measuring the capacitance at the first capacitor 110, measuring the capacitance at the second capacitor 120, and subtracting one capacitance from the other. In one embodiment, subtractor 185 performs the subtraction. Additionally, the differential capacitance may be correlated to a gas volume value based in part on the fluid line bore diameter. Such gas volume values may be stored in memory 175, for example, in a lookup table.

Figure 3:
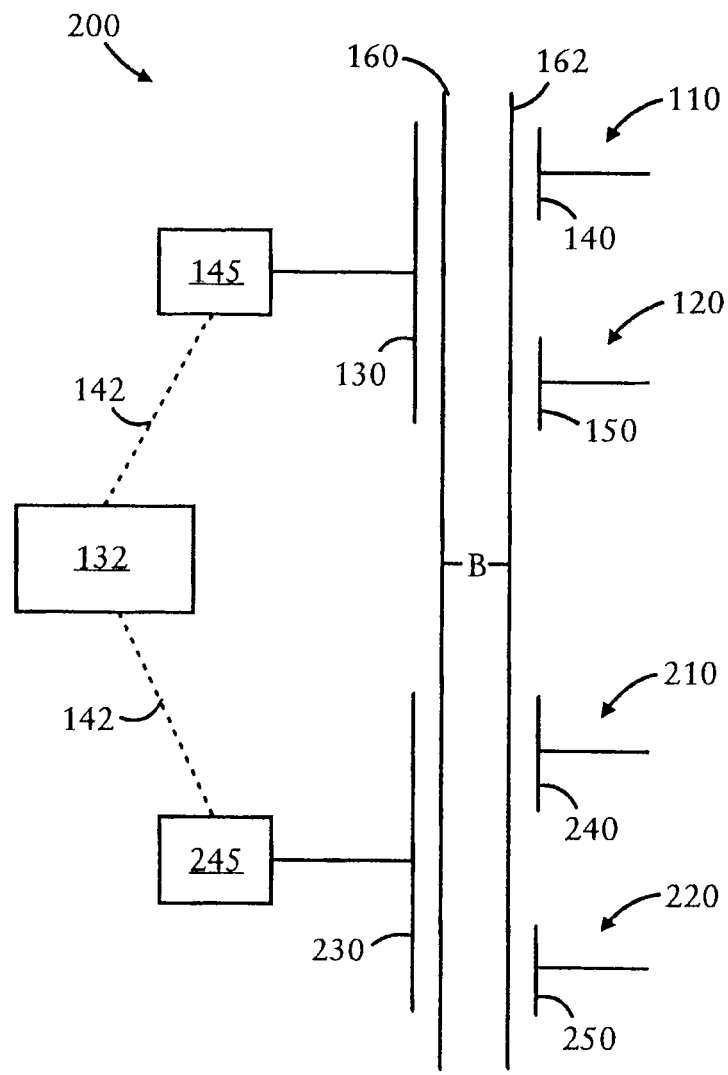
FIG. 3 is a schematic depiction of a fluid monitoring system, according to certain disclosed embodiments.

Referring now to FIG. 3, in this example, first capacitor 110, second capacitor 120, a third capacitor 210, and a fourth capacitor 220 comprise another embodiment of a fluid monitoring system 200. First and second capacitors 110, 120 operate in the same manner as described with respect to FIG. 2. In this example, third capacitor 210 operates similarly to first capacitor 110 and fourth capacitor 220 operates similarly to second capacitor 120. Accordingly, third capacitor 210 includes a first plate 230 and a second plate 240 and fourth capacitor 220 includes the first plate 230 and a third plate 250.

Similar to FIG. 2, capacitors 210 and 220 are connected to a capacitance-to-digital converter 145 and 245, respectively. In some embodiments, the capacitance-to-digital converters 145, 245 are in communication with a shared electrical circuit 132. In other embodiments, capacitance-to-digital converters 145, 245 are in communication with separate electrical circuits.

In the system shown in FIG. 3, having four capacitors 110, 120, 210, 220, a plurality of differential capacitances may be determined. For example, a first differential capacitance between capacitors 110 and 120 may be determined and a second differential capacitance between capacitors 210 and 220 may also be determined. As mentioned above, multiple capacitance measurements may aid to preserve the integrity of the capacitance signals. Furthermore, multiple differential capacitance measurements may aid in determining the contents of the fluid in fluid line 160, particularly the flow of such contents.

In certain embodiments, the differential capacitance is useful in determining the size of gas bubbles and whether gas bubbles are moving along the length of the fluid line 160. For example, if a capacitance is detected at capacitor 110, which is not equal to the reference capacitance, thereby indicating that there is gas in the fluid line at capacitor 110, and a similar capacitance is detected at capacitor 120 moments later, it may be presumed that gas bubbles are moving through the fluid line 160. If, however, a similar capacitance is not detected at capacitor 120 moments later, it may be presumed that gas bubbles are not moving through the fluid line 160 with the fluid, but rather may be relatively stationary in the fluid line 160 as the fluid continues to flow.

Furthermore, if a capacitance is detected simultaneously at capacitors 110 and 120, which is not equal to the reference capacitance, and which does not change reasonably quickly, it may be presumed that either a large bubble is being detected that is not moving through fluid line 160 with the fluid or a large amount of gas is moving through the fluid line 160. Therefore, it should be appreciated that the relative placement of the capacitors 110 and 120 is important because the space they occupy and the distance between them define a capacitance monitoring distance, which may or may not be able to detect a particular size gas bubble. Therefore, capacitors 110 and 120 should be spaced apart a predetermined distance (a capacitance monitoring distance) in order to detect a desired gas bubble size. In an exemplary embodiment, capacitors 110 and 120 are separated by a distance of greater than or equal to 8 mm. In an exemplary embodiment, the system shown in FIG. 3 may have an overall length of 50 mm, including all four capacitors 110, 120, 210, 220 and the spaces between them.

Figure 6:
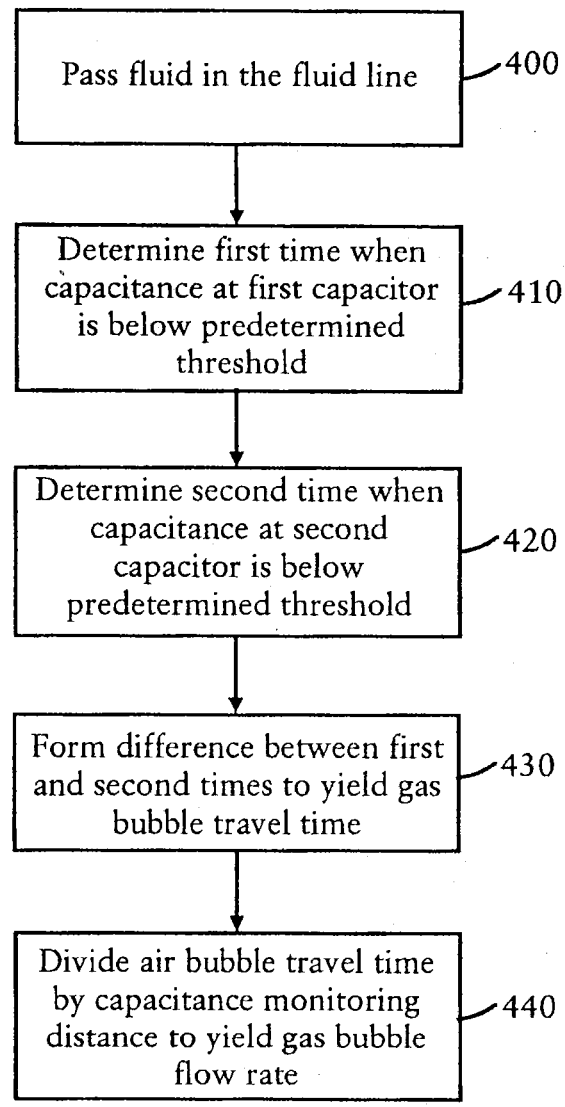
FIG. 6 is a flowchart showing a method for determining gas bubble flow rate in a fluid line, according to certain disclosed embodiments.

Referring now to FIGS. 3 and 6, a method is shown for determining a gas bubble flow rate in a fluid line. At step 400, fluid is permitted to flow in the fluid line 160. At step 410, a first time at which the capacitance at first capacitor 110 falls below a threshold is determined. At step 420, a second time at which the capacitance at second capacitor 120 falls below a threshold is determined. The times at which the capacitances fall below a threshold is determined by sensing the capacitance at a capacitor, comparing the sensed capacitance at the capacitor with a reference capacitance, and if the sensed capacitance at the capacitor is below the reference capacitance, recording the sensed capacitance value and referencing the sensed capacitance value to the time of occurrence. In one embodiment, comparator 180 performs the capacitance comparison. In one embodiment, the sensed capacitance value is stored in memory 175. In one embodiment, the time of occurrence is provided by clock 195.

At step 430, the second time is subtracted from the first time or alternatively, the first time is subtracted from the second time, to yield a gas bubble travel time. At step 440 the gas bubble travel time is divided by the capacitance monitoring distance to yield a gas bubble flow rate. The division of capacitance monitoring distance by gas bubble travel time may be performed by divider 190. This gas bubble flow rate provides information pertaining to whether or not gas is flowing at the same rate as fluid in the line. As mentioned above, this information is useful because accurate indications of bubble volume may be determined, thereby minimizing the number of false or nuisance alarms generated.

Additionally, if a bubble size is detected which is deemed to be problematic, i.e., exceeds a desired bubble size, the fluid line 160 may then be purged. Alternatively, if the bubble flow rate is undesirable, i.e., is too slow or too fast, the fluid line 160 may then be purged. This purging or expelling the contents of fluid line 160 ensures that a patient does not receive fluid with entrained dangerous bubbles.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. For example, any suitable comparator may be used in comparing the sensed in-line capacitance with a reference capacitance. Similarly, any suitable subtractor may be used in determining the differential capacitance. Thus, the present invention is not intended to be limited to the embodiments shown herein but is to be accorded the widest scope consistent with the principles and novel features disclosed herein.

What is claimed is:

1. An apparatus for monitoring the amount of gas in a fluid in a fluid line, comprising:
    a first capacitor comprising a first plate and a second plate, the first and second plates being separated by and positioned on opposing sides of the fluid line such that fluid moving through the fluid line passes between the first and second plates, wherein the first capacitor is configured to sense the capacitance of the fluid line;
    a reference capacitance equal to the capacitance of the first capacitor while an initializing fluid from which all gas has been purged is in the fluid line;
    a processor in communication with the first capacitor,
    wherein the processor is configured to compare the sensed capacitance at the first capacitor with the reference capacitance to determine whether there is gas present in the fluid in the fluid line.

2. The apparatus of claim 1, further comprising a predetermined threshold equal to the capacitance of the first capacitor while a fluid comprising a maximum acceptable content of gas is in the line, wherein the processor is configured to compare the sensed capacitance at the first capacitor with the predetermined threshold and to trigger an alarm if the sensed capacitance is less than the predetermined threshold.

3. The apparatus of claim 2, wherein the predetermined threshold is less than the reference capacitance and greater than the capacitance at the first capacitor when only gas is in the line.

4. The apparatus of claim 1, further comprising:
    a capacitance-to-digital converter in communication with the first capacitor.

5. The apparatus of claim 4, wherein the fluid being monitored is a medical fluid.

6. The apparatus of claim 1, wherein the processor is further configured to correlate the sensed capacitance at the first capacitor when it falls below a threshold with a gas volume based in part on the fluid line bore diameter to determine gas bubble size.

7. The apparatus of claim 1, further comprising:
    a second capacitor comprising the first plate and a third plate, the first and third plates being separated by and positioned on opposing sides of the fluid line such that fluid moving through the fluid line passes between the first and third plates;
    wherein the second capacitor is configured to sense the capacitance of the fluid line and wherein the processor is configured to compare the sensed capacitance at the second capacitor with a reference capacitance to determine the composition of the fluid in the fluid line.

8. The apparatus of claim 7, wherein the processor is further configured to subtract the capacitance sensed one capacitor from the capacitance sensed at the other capacitor to yield a differential capacitance and to compare the differential capacitance with the reference capacitance to determine whether there is gas present in the fluid in the fluid line.

9. The apparatus of claim 7, further comprising:
    a capacitance-to-digital converter in communication with the first capacitor and the second capacitor.

10. The apparatus of claim 7, wherein the second and third plates are separated from each other by a distance of greater than 8 mm.

11. The apparatus of claim 7, wherein the processor is further configured to correlate the sensed capacitance at the first capacitor when it falls below a first threshold with a first time, wherein the processor is configured to correlate the sensed capacitance at the second capacitor when it falls below the first threshold with a second time, and wherein the processor is configured to determine gas bubble size based in part on the fluid line bore diameter and difference in time between the first capacitor falling below the first threshold at the first time and the second capacitor falling below the first threshold at the second time.

12. A method for determining whether gas is present in a fluid being monitored in a fluid line, comprising:
    passing a first initializing fluid from which all gas has been purged through a fluid line, wherein the fluid line is at least partially surrounded by a first capacitor;
    sensing the capacitance of the fluid line at the first capacitor while the first initializing fluid is in the line;
    saving the sensed capacitance while the first initializing fluid is in the line as a reference capacitance;
    passing a fluid to be monitored through the fluid line;
    sensing the capacitance of the fluid line at the first capacitor while the fluid to be monitored is in the line;
    comparing with a processor the sensed capacitance while the fluid to be monitored is in the line with the reference capacitance; and
    determining that gas is present in the fluid to be monitored when the sensed capacitance while the fluid to be monitored is in the line is less than the reference capacitance.

13. The method of claim 12, further comprising:
    passing a second initializing fluid comprising a maximum acceptable content of gas through the fluid line;
    sensing the capacitance of the fluid line at the first capacitor while the second initializing fluid is in the line;
    saving the sensed capacitance while the second initializing fluid is in the line as a threshold; and
    triggering an alarm if the sensed capacitance while the fluid to be monitored is in the line is below the threshold.

14. The method of claim 12, wherein the fluid line is at least partially surrounded by a second capacitor.

15. The method of claim 14, further comprising:
sensing the capacitance of the fluid line at the second capacitor;
comparing the sensed capacitance at the second capacitor with a reference capacitance; and
determining whether gas is present in the fluid line based on the comparing of the sensed capacitance at the second capacitor to the reference capacitance.

16. The method of claim 15, further comprising:
subtracting the capacitance sensed one capacitor from the capacitance sensed at the other capacitor to yield a differential capacitance.

17. An apparatus for monitoring the amount of air in a fluid in a fluid line, comprising:
a first capacitor comprising a first plate and a second plate, the first and second plates being separated by and positioned on opposing sides of the fluid line such that fluid moving through the fluid line passes between the first and second plates;
a processor in communication with the first capacitor;
wherein the first capacitor is configured to sense the capacitance of the fluid line and wherein the processor is configured to compare the sensed capacitance at the first capacitor with a reference capacitance and to determine, when the sensed capacitance is less than the reference capacitance, that air is present in the fluid in the fluid line,
wherein the reference capacitance is a capacitance of the first capacitor established with the fluid line filled with an initializing fluid from which all air has been purged during an initial setup mode.

18. The apparatus of claim 17, wherein the processor is further configured to compare the sensed capacitance at the first capacitor with a predetermined threshold and to trigger an alarm if the sensed capacitance is less than the predetermined threshold, wherein the predetermined threshold is equal to the capacitance of the first capacitor while a fluid comprising an accepted maximum content of gas is in the line.

19. The apparatus of claim 17, wherein the reference capacitance is stored in a memory and accessed by the processor during a normal mode of operation for comparison to the sensed capacitance.

* * * * *